United States Patent [19]

Winkler et al.

[11] Patent Number: 5,202,512
[45] Date of Patent: Apr. 13, 1993

[54] PROCESS FOR THE PREPARATION OF HALOGENOALKANES

[75] Inventors: Peter-Paul Winkler, Kastl; Ulrich Goetze, Burghausen, both of Fed. Rep. of Germany

[73] Assignee: Wacker-Chemie GmbH, Munich, Fed. Rep. of Germany

[21] Appl. No.: 830,474

[22] Filed: Feb. 3, 1992

Related U.S. Application Data

[63] Continuation of Ser. No. 594,846, Oct. 9, 1990, abandoned.

[30] Foreign Application Priority Data

Nov. 16, 1989 [DE] Fed. Rep. of Germany ....... 3938089

[51] Int. Cl.$^5$ .............................................. C07C 17/16
[52] U.S. Cl. .................................................. 570/258
[58] Field of Search .......................................... 570/258

[56] References Cited

U.S. PATENT DOCUMENTS

| 2,908,725 | 4/1957 | Butterfield et al. | 570/258 |
| 3,852,368 | 12/1974 | Boggs | 260/657 |
| 3,981,938 | 9/1976 | Steele et al. | 260/657 |

FOREIGN PATENT DOCUMENTS

| 34646 | 10/1969 | Japan | 570/258 |
| 28885 | 9/1973 | Japan | 570/258 |
| 150026 | 4/1980 | Japan | 570/258 |
| 126428 | 1/1981 | Japan | 570/258 |

OTHER PUBLICATIONS

Soviet Inventions Illustrated, CH Section, Week C 34, Oct. 1, 1980 Derwent Publications Ltd., London, C03, SU-707 904 (Vershinin).
Soviet Inventions Illustrated, CH Section, Week C 33, Sept. 24, 1980 Derwent Publications Ltd., London, C01, SU-706 391 (Troitskii).
Patent Abstracts of Japan, unexamined applications, C Section, vol. 3, No. 50, Apr. 27, 1979, The Patent Office Jap. Government, p. 20, C44 Kokai-No. 50, 54-24 803 (Shin Nippon Rika).
Patent Abstracts of Japan, unexamined applications, C Section, vol. 6, No. 31, Feb. 24, 1982, The Patent Office Jap. Government, p. 94, C92, Kokai-No. 56-150 026 (Shinetsu).
Patent Abstracts of Japan, unexamined applications, C Section, vol. 7, No. 219, Sep. 29, 1983, The Patent Office Japanese Government, p. 165, C 188, Kokai-No. 58-118 526 (Mitsubishi Gas).
EP0257866—WPI Abstract.
US 8918 U.S. Pat. No. 4,822,928 WPI Abstract.
EP 9010 EP0257866 WPI Abstract.
Basic JP62005930 WPI Abstract.

Primary Examiner—Marianne M. Cintins
Assistant Examiner—Kimberly J. Kesner
Attorney, Agent, or Firm—Burgess, Ryan & Wayne

[57] ABSTRACT

Process for the preparation of methyl chloride, which comprises reacting methanol with hydrogen chloride in a concentration below the particular ageotropic concentration in the liquid phase in the presence of an amine hydrohalide.

16 Claims, 1 Drawing Sheet

PROCESS FOR THE PREPARATION OF HALOGENOALKANES

This application is a continuation of application Ser. No. 594,846, filed Oct. 9, 1990, now abandoned.

FIELD OF THE INVENTION

The invention relates to a process for the preparation of halogenoalkanes having 1 to 4 carbon atoms in the presence of an amine hydrohalide.

BACKGROUND OF THE INVENTION

Many processes for the preparation of halogenoalkanes are known. These are essentially catalyzed and non-catalyzed processes in the gas phase or liquid phase. U.S. Pat. No. 3,981,938, for example, describes the preparation of halogenoalkanes in the liquid phase by reaction of an alkanol with at least a 10% excess of hydrogen halide, the water of reaction obtained being removed at the bottom of the liquid phase reactor as a mixture with alkanol and hydrogen halide. A similar process is known from U.S. Pat. No. 3,983,180, in which methanol is reacted with hydrogen chloride in the liquid phase to give methyl chloride, the concentration of the hydrogen chloride being above the azeotrope concentration. Both processes have the disadvantage that working up of the aqueous solution of hydrogen halide removed from the circulation is cost-intensive and associated with a high expenditure on apparatus.

U.S. Pat. No. 4,366,324 describes a process for the simultaneous preparation of organosiloxanes and methyl chloride from an organochlorosilane and methanol in the liquid phase, the concentration of the hydrogen chloride in the liquid phase being below the azeotrope concentration. The disadvantages of this process lie chiefly in the comparatively low space-time yield and in the relatively high content of the by-product dimethyl ether, which additionally makes purification of the methyl chloride more difficult.

U.S. Pat. No. 4,108,882 discloses a process for the simultaneous preparation of siloxanes and methyl chloride in the gas phase, in which an organochlorosilane and methanol are reacted in the presence of a quaternary ammonium compound as the catalyst, the temperatures and pressure being chosen so that the water formed can escape from the reaction zone, in order to avoid deactivation of the catalyst.

The object of the present invention is to provide a process which enables halogenoalkanes to be prepared in a relatively simple manner and with a high space-time yield, in which the formation of by-products are reduced to a minimum.

SUMMARY OF THE INVENTION

The invention relates to a process for the preparation of halogenoalkanes having 1 to 4 carbon atoms, which comprises reacting an alkanol having 1 to 4 carbon atoms with a hydrogen halide in the liquid phase in the presence of at least one amine hydrohalide.

The amine hydrohalides employed in the process according to the invention are preferably amine hydrochlorides and hydrobromides, most preferably, amine hydrochlorides. The amines may be primary, secondary or tertiary, linear or cyclic, aliphatic or aromatic amines, with the priviso that the amine hydrohalides employed according to the invention have an adequate heat stability and are preferably partly soluble, most preferably, completely soluble, in the liquid phase, at a temperature of 25° C.

Examples of amines which form the amine hydrohalides employed according to the invention are ammonia, methylamine, trimethylamine, diethylamine, triethylamine, n-butylamine, tributylamine, ethylenediamine, 1-4,diazabicyclo(2,2,2)-octane, 3-dimethylaminopropylamine, diethylenetriamine, aniline and anilines substituted by halogen atoms and/or alkyl groups, such as N,N-dimethylaniline, o-, m- or p-phenylenediamine, heterocyclic amine compounds, such as quinoline, imidazoles, piperidines and piperazines, and pyridine and substituted pyridines, such as pyridines substituted by halogen atoms, alkyl groups and/or amino groups.

Preferred amines which form the amine hydrohalides employed according to the invention are the aromatic amines, such as, for example, anilines, pyridines, quinolines, phenylenediamines and alpha- and beta-naphthylamine. Aromatic amines having a low molecular weight are particularly preferred.

Examples of the amine hydrohalides which are preferably employed in the process according to the invention are the hydrochlorides of pyridine, 2-methylpyridine, 4-methylpyridine and aniline.

The amine hydrohalides employed in the process according to the invention can be introduced into the reactor such as, for example, as a mixture with water, or prepared in the reactor from the corresponding amine by reaction with a hydrogen halide.

The amine hydrohalide employed in the process according to the invention can be a single type or a mixture of at least two types of such amine hydrohalides.

In the process according to the invention, the liquid phase contains the amine hydrohalide in amounts of preferably about 10 to 80 percent by weight, most preferably, about 35 to 60 percent by weight, based on the total weight of the liquid phase and in each case calculated as the weight of free amine.

Examples of the alkanol employed in the process according to the invention are methanol, ethanol, n-propanol, isopropanol, n-butanol, sec.-butanol and tert.-butanol.

Methanol, ethanol, propanol and isopropanol are preferably employed as the alkanol in the process according to the invention, methanol being particularly preferred.

The alkanol is employed in the process according to the invention in amounts such that the concentration of alkanol in the liquid phase is preferably between about 0.5 and 10 percent by weight, most preferably, between about 0.5 and 4 percent by weight, in each case based on the total weight of the liquid phase.

The hydrogen halide employed in the process according to the invention is preferably hydrogen chloride or bromide, hydrogen chloride being particularly preferred.

The hydrogen halide is employed in the process according to the invention in amounts such that the concentration of free hydrogen halide in the liquid phase is preferably below the particular azeotrope concentration. The concentration of free hydrogen halide in the liquid phase is preferably between about 0.1 and 19 percent by weight, most preferably, between about 0.1 and 10 percent by weight, in each case based on the total weight of the liquid phase. The hydrogen halide not bonded to the amine is designated as the free hydrogen halide.

In the process according to the invention, the reaction is carried out at a temperature of preferably about 90° to 200° C., most preferably, about 100° to 160° C., under a pressure of preferably about 900 to 16,000 hPa, most preferably about 1,000 to 6,000 hPa, the reaction conditions preferably being chosen so that the volume of the liquid phase remains approximately constant.

For carrying out the process according to the invention, the alkanol and hydrogen halide are introduced into a reactor containing the amine hydrohalide as a mixture with water and, if appropriate, other substances. The alkanol and hydrogen halide can in each case be added either in the liquid or in the gaseous state, as gas/liquid mixtures or in the form of aqueous solutions. The halogenoalkane formed in the reaction is isolated in a manner which is known, per se.

BRIEF DESCRIPTION OF THE DRAWING

The following drawing is illustrative of an embodiment of the invention and is not intended to limit the invention as encompassed by the claims forming part of the application.

Figure 1:
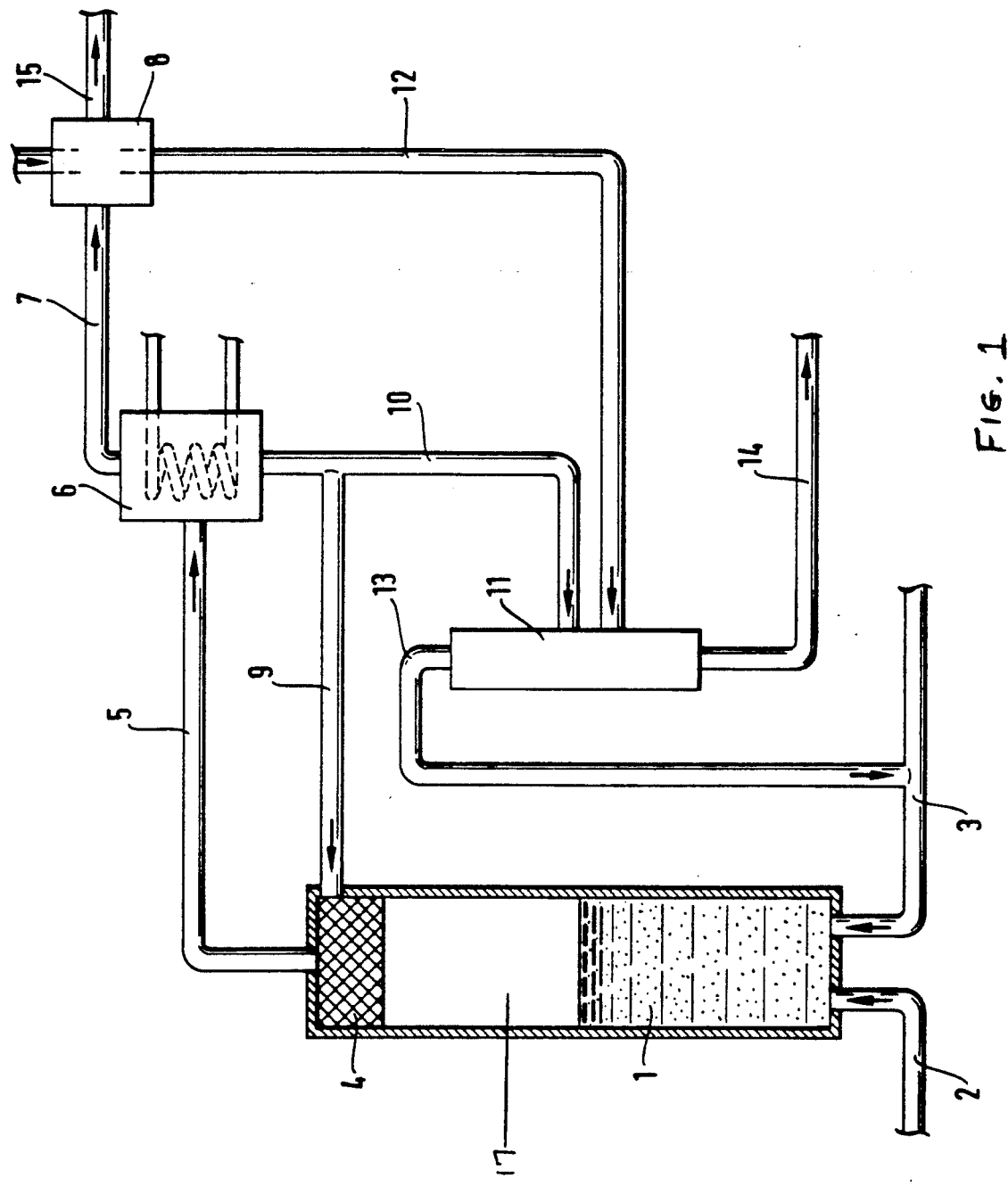
FIG. 1 is a schematic view of an embodiment of the invention.

A preferred embodiment of the process according to the invention is illustrated with the aid of FIG. 1 and using hydrogen chloride and methanol as starting substances.

Hydrogen chloride is fed via line (2) and methanol is fed via line (3) into a reactor (1) which can be heated and contains the catalyst as a mixture with water. The methyl chloride formed in the reaction escapes as a mixture with water, methanol and traces of hydrogen chloride into the gas space 17 and passes via line (5) into the condenser (6), where most of the water and methanol are removed and are fed via line (10) to the distillation column (11). The methanol obtained at the top of the distillation column (11) is fed via line (13) into the reactor (1), while the water contained in the bottom product of the distillation column (11) leaves the unit via line (14). The methyl chloride is fed from the condenser (6) via line (7) to the water washer (8), an absorption column in which the methyl chloride is freed from the methanol by being brought into contact with water, via line 16 and leaves the unit via line (15). The methanol-containing water from the water washer (8) is likewise fed to the distillation column (11) via line (12).

In a particularly preferred embodiment of the process according to the invention, packed column packing (4) into which the condensate containing the methanol and water can be recycled from the condenser (6) via line (9) is located at the top of the reactor (1), the gas mixture leaving the reactor (1) being brought into contact with the recycling condensate. The ratio of the amount of condensate recycled via line (9) to the amount of condensate fed via line (10) into the distillation column (11) is preferably between 0 and 2, most preferably, between 0 and 1 in this embodiment.

One advantage of the process according to the invention is that halogenoalkanes can be prepared in a relatively simple manner and with a high space-time yield. In addition, no by-products, or only a very small amount of by-products such as, for example, dialkyl ether, are formed. High rates of reaction and a very low discharge of alkanol and hydrogen halide with the reaction products are characteristic of the process according to the invention.

In the examples described below, all the data designating parts and percentages relate to weight, unless stated otherwise. The ratio of the amount of condensate recycled via line (9) to the amount of condensate fed via line (10) into the distillation column (11) is designated in the reflux ratio below. The space-time yield designates the flow of product in weight based on the unit volume of the liquid phase ($kg/m^3 \times h$).

EXAMPLE 1

Reactor (1) contains a glass tube having a length of 1,500 mm and an internal diameter of 50 mm. A circulatory evaporator operated with quartz heating bars is flanged onto the tube. The top of the glass tube is filled with a packed column layer 300 mm high (BERL saddles of ceramic, 6×6 mm) (4). A solution of 3-dimethylaminopropylamine hydrochloride in water, prepared by introducing 622 g of hydrogen chloride into a solution of 1.169 g of water and 557 g of 3-dimethylaminopropylamine, was introduced into reactor (1) and brought to the boiling point under a pressure of 1,600 hPa.

After feeding of hydrogen chloride via line (2) and methanol via line (3) was started, a flow equilibrium was established, which is characterized as follows. The reflux ratio was 1.0.

| FEED | |
|---|---|
| Hydrogen chloride (2): | 461 g/h |
| Methanol (3): | 560 g/h |
| LIQUID PHASE | |
| Volume: | 2.2 l |
| Temperature: | 118° C. |
| Concentration of free hydrogen chloride: | 9.2% |
| Concentration of methanol: | 3.0% |
| Concentration of the 3-dimethylaminopropylamine hydrochloride, calculated as the weight of free amine: | 23.0% |
| DISCHARGE (5) | |
| Hydrogen chloride: | 0.19 g/h |
| Methanol: | 156 g/h |
| Water: | 227 g/h |
| Methyl chloride: | 132 g/h |
| Dimethyl ether: | 0.5 g/h |

The space-time yield is 290 $kg/m^3 \times h$ of methyl chloride.

EXAMPLE 2

A solution of pyridine hydrochloride in water, prepared by passing 588 g of hydrogen chloride into a solution of 816 g of water and 968 g of pyridine was introduced into the reactor (1) described in Example 1 and brought to the boiling point under a pressure of 1,600 hPa.

After the feeding of hydrogen chloride via line (2) and methanol via line (3) was started, a flow equilibrium was established, which is characterized as follows. The reflux ratio was 0.3.

| FEED | |
|---|---|
| Hydrogen chloride (2): | 668 g/h |
| Methanol (3): | 800 g/h |
| LIQUID PHASE: | |
| Volume: | 2.2 l |
| Temperature: | 126° C. |
| Concentration of free hydrogen chloride: | 5.8% |
| Concentration of methanol: | 2.0% |
| Concentration of the pyridine hydrochloride, calculated as the weight of free amine: | 40.0% |

-continued

DISCHARGE (5)
| | |
|---|---|
| Hydrogen chloride: | 0.36 g/h |
| Methanol: | 214 g/h |
| Water: | 329 g/h |
| Methyl chloride: | 191 g/h |
| Dimethyl ether: | 0.2 g/h |

The space-time yield is 420 kg/m$^3$×h of methyl chloride.

EXAMPLE 3

A solution of pyridine hydrochloride in water, prepared by passing 595 g of hydrogen chloride into a solution of 525 g of water and 1.234 g of pyridine was introduced into the reactor (1) described in Example 1 and brought to the boiling point under a pressure of 1,600 hPa.

After feeding of hydrogen chloride via line (2) and methanol via line (3) was started, a flow equilibrium was established, which is characterized as follows. The reflux ratio was 1.0.

| FEED | |
|---|---|
| Hydrogen chloride (2): | 1,280 g/h |
| Methanol (3): | 874 g/h |
| LIQUID PHASE: | |
| Volume: | 2.2 l |
| Temperature: | 125° C. |
| Concentration of free hydrogen chloride: | 1.1% |
| Concentration of methanol: | 2.7% |
| Concentration of the pyridine hydrochloride, calculated as the weight of free amine: | 51.0% |
| DISCHARGE (5) | |
| Hydrogen chloride: | 0.24 g/h |
| Methanol: | 513 g/h |
| Water: | 431 g/h |
| Methyl chloride: | 250 g/h |
| Dimethyl ether: | 0.3 g/h |

The space-time yield is 550 kg/m$^3$×h of methyl chloride.

COMPARISON EXAMPLE 1

3.1 l of a solution consisting of 80% of water, 16% of hydrogen chloride and 4% of methanol were introduced into the reactor (1) described in Example 1 and brought to the boiling point under a pressure of 1,600 hPa.

After feeding of hydrogen chloride via line (2) and methanol via line (3) was started, a flow equilibrium was established, which is characterized as follows. The reflux ratio here is 1.6.

| FEED | |
|---|---|
| Hydrogen chloride (2): | 291 g/h |
| Methanol (3): | 375 g/h |
| LIQUID PHASE: | |
| Volume: | 3.1 l |
| Temperature: | 116° C. |
| Concentration of free hydrogen chloride: | 16.6% |
| Concentration of methanol: | 3.9% |
| DISCHARGE (5) | |
| Hydrogen chloride: | 5 mg/h |
| Methanol: | 120 g/h |
| Water: | 144 g/h |
| Methyl chloride: | 42 g/h |
| Dimethyl ether: | 0.3 g/h |

The space-time yield is 130 kg/m$^3$×h of methyl chloride.

What is claimed is:

1. A process for the preparation of methyl chloride which comprises reacting methanol with hydrogen chloride in a concentration below the particular azeotropic concentration in the liquid phase in the presence of an amine hydrohalide selected from the group consisting of hydrochlorides of an aromatic amine.

2. The process of claim 1, wherein the methanol is present in an amount of about 0.5 to 10 percent by weight based on the total weight of the liquid phase.

3. The process of claim 1, wherein the aromatic amine hydrochloride is selected from the group consisting of pyridine hydrochloride, 2-methyl pyridine hydrochloride, 4-methyl pyridine hydrochloride and aniline hydrochloride.

4. The process of claim 1, wherein the liquid phase contains the amine hydrohalide in an amount of about 10 to 80 percent by weight, based on the total weight of the liquid phase and calculated as the weight of free amine.

5. The process of claim 4, wherein the liquid phase contains the amine hydrohalide in an amount of about 35 to 60 percent by weight.

6. The process of claim 1, wherein the concentration of hydrogen chloride is between about 0.1 and 19 percent by weight based on the total weight of the liquid phase.

7. The process of claim 1, wherein the reaction is conducted at a temperature of between about 9° and 200° C.

8. The process of claim 7, wherein the reaction is conducted at a temperature of between about 100° and 160° C.

9. The process of claim 1, wherein the reaction is conducted under a pressure of between about 900 and 16,000 hPa.

10. The process of claim 9, wherein the reaction is conducted at a pressure between about 1,000 and 6,000 hPa.

11. A process for the preparation of methyl chloride which comprises reacting methanol in an amount of about 0.5 to 10 percent by weight with hydrogen chloride in a concentration below the particular azeotrope concentration in the liquid phase in the presence of an aromatic amine hydrochloride in an amount of about 35 to 60 percent by weight based on the total weight of the liquid phase and calculated as the weight of free amine, at a temperature of from about 100° to 160° C. and a pressure of from about 1,000 to 6,000 hPa.

12. The process of claim 11, wherein the concentration of the hydrogen chloride is between about 0.1 and 19 percent by weight based on the total weight of the liquid phase.

13. The process of claim 11, wherein the aromatic amine hydrochloride is selected from the group consisting of pyridine hydrochloride, 2-methyl pyridine hydrochloride, 4-methyl pyridine hydrochloride and aniline hydrochloride.

14. A continuous process for the preparation of methyl chloride which comprises introducing methanol and hydrogen chloride into a reactor containing an aqueous solution of an aromatic amine hydrochloride wherein the concentration of methanol in the liquid phase is between about 0.5 and 10 percent by weight based on the total weight of the liquid phase, the concentration of free hydrogen chloride in the liquid phase is below the azetotropic concentration and between 0.1 and 19 percent by weight, the amine hydrohalide is present in an amount of about 10 to 80 percent by weight, based on the total weight of the liquid phase and calculated as the weight of free amine, and the reactor is maintained at a temperature of from about 100° to 160° C. and at a pressure of from about 1000 to 6000 hPa; withdrawing from the gas space of the reactor a gaseous mixture of methyl chloride, water and methanol, separating methyl chloride from the mixture by condensing the water and methanol, washing the separated methyl chloride with water to remove any residual methanol and thereafter recovering the methyl chloride.

15. The process of claim 14 wherein the water and methanol condensed from the mixture is recycled to the gas space of the reactor and brought into contact with the gaseous mixture leaving the reactor.

16. The process of claim 14 wherein the water and methanol condensed from the mixture is distilled and the methanol distillate recycled into the reactor.

* * * * *